(12) United States Patent
Meßner

(10) Patent No.: US 11,648,105 B2
(45) Date of Patent: May 16, 2023

(54) OPHTHALMOLOGICAL IMPLANT

(71) Applicant: HumanOptics Holding AG, Erlangen (DE)

(72) Inventor: Arthur Meßner, Schnaittach (DE)

(73) Assignee: HUMANOPTICS HOLDING AG, Erlangen (DE)

( * ) Notice: Subject to any disclaimer, the term of this patent is extended or adjusted under 35 U.S.C. 154(b) by 636 days.

(21) Appl. No.: 16/302,411

(22) PCT Filed: May 15, 2017

(86) PCT No.: PCT/EP2017/061628
§ 371 (c)(1),
(2) Date: Nov. 16, 2018

(87) PCT Pub. No.: WO2017/198627
PCT Pub. Date: Nov. 23, 2017

(65) Prior Publication Data
US 2019/0201187 A1 Jul. 4, 2019

(30) Foreign Application Priority Data

May 17, 2016 (DE) ...................... 10 2016 208 395.3

(51) Int. Cl.
*A61F 2/14* (2006.01)
*B29D 11/00* (2006.01)
*B29D 11/02* (2006.01)

(52) U.S. Cl.
CPC .......... *A61F 2/15* (2015.04); *B29D 11/00317* (2013.01); *B29D 11/023* (2013.01); *A61F 2240/002* (2013.01)

(58) Field of Classification Search
CPC ................ A61F 2/15; A61F 2240/002; B29D 11/00317; B29D 11/023
See application file for complete search history.

(56) References Cited

U.S. PATENT DOCUMENTS

| 3,679,504 | A | 7/1972 | Wichterle | |
| 5,070,166 | A * | 12/1991 | Su | ........................ G02B 1/043 526/301 |
| 6,221,106 | B1 | 4/2001 | Hermeking | |
| 9,005,281 | B2 * | 4/2015 | Christie | ........... B29D 11/00317 623/6.17 |
| 9,329,410 | B2 | 5/2016 | Riall et al. | |
| 2008/0304009 | A1 * | 12/2008 | Thomas | ........... B29D 11/00038 351/159.24 |

(Continued)

FOREIGN PATENT DOCUMENTS

| CN | 102 090 941 B | 1/2016 |
| DE | 26 52 646 A1 | 5/1978 |
| DE | 198 50 807 A1 | 5/2000 |

(Continued)

*Primary Examiner* — Jerrah Edwards
*Assistant Examiner* — Christine L Nelson
(74) *Attorney, Agent, or Firm* — McGlew and Tuttle, P.C.

(57) ABSTRACT

An ophthalmological implant includes a main structure with a central aperture, a first side, and a second side arranged opposite the first side. It further includes a plurality of pigment arrangements arranged in the main structure, at least one of the pigment arrangements includes at least one color pigment and an enclosure that encloses at least most of the at least one color pigment.

18 Claims, 2 Drawing Sheets

(56) References Cited

U.S. PATENT DOCUMENTS

2011/0040376 A1* 2/2011 Christie ........... B29D 11/00317
623/6.17
2016/0243131 A1* 8/2016 Hughes ................ A61K 9/0051

FOREIGN PATENT DOCUMENTS

| DE | 10 2007 042 637 A1 | 3/2009 |
|----|---------------------|--------|
| GB | 1592485 A | 7/1981 |
| KR | 20140113534 A | 9/2014 |
| RU | 2513681 C1 | 4/2014 |
| RU | 2526245 A | 9/2014 |

* cited by examiner

OPHTHALMOLOGICAL IMPLANT

CROSS REFERENCE TO RELATED APPLICATIONS

This application is a United States National Phase Application of International Application PCT/EP2017/061628 filed May 15, 2017 and claims the benefit of priority under 35 U.S.C. § 119 of German Patent Application Serial No. DE 10 2016 208 395.3 filed on May 17, 2016, the entire contents of which are incorporated herein by reference.

FIELD OF THE INVENTION

The invention concerns an ophthalmological implant, which is often also referred to as iris implant. The invention is further directed at a method of producing a pigment arrangement as a component of an ophthalmological implant of this type.

BACKGROUND OF THE INVENTION

In order to replace a partly or completely missing iris, it is common practice nowadays to use circumferentially tinted contact lenses or ophthalmological implants. An ophthalmological implant of the generic type is known from DE 10 2007 042 637 A1, for example. This ophthalmological implant has proven well in practical application.

It is known to produce ophthalmological implants with one or with different external diameters. To adapt the ophthalmological implant to be implanted to individual anatomical conditions of an eye to be treated, or a partial aniridia to be treated, the ophthalmological implant is usually reduced in its external diameter. This may be done, for example, with a trepan, a pair of scissors or a scalpel. The drawback thereof is that this usually impairs the biocompatibility of the ophthalmological implant.

SUMMARY OF THE INVENTION

Therefore, the invention is based on the object of providing an ophthalmological implant, which is able to alleviate the prior art drawbacks. In particular, the aim is to provide an ophthalmological implant, which offers exceptional biocompatibility even after adapting the same to the individual anatomical conditions of the eye to be treated or the aniridia to be treated. A corresponding method of producing pigment arrangements as components of an ophthalmological implant of this type is to be provided as well.

According to the invention, this object is achieved by an ophthalmological implant comprising a main structure with a central aperture, a first side and a second side arranged opposite the first side, and a plurality of pigment arrangements arranged in the main structure, wherein at least one of the pigment arrangements has at least one color pigment, and an enclosure enclosing at least most of the at least one color pigment.

Furthermore, this object is achieved by a method for producing pigment arrangements as a component of an ophthalmological implant according to the invention, the method comprising the steps of providing at least one color pigment, providing enclosure material, in particular of biocompatible material, and dispersing the at least one color pigment in the enclosure material to form a pigment arrangement with the at least one enclosed color pigment.

The gist of the invention is that at least most of the at least one color pigment of the pigment arrangement is enclosed by an enclosing material. This ensures that the at least one color pigment of the pigment arrangement is in particular sealed off, in other words encapsulated, which improves the biocompatibility of the ophthalmological implant, in particular even after adapting the latter.

Favorably, at least one of, more preferably a plurality of, more preferably most, more preferably all of the pigment arrangements has at least one enclosing color pigment.

It is advantageous if the at least one pigment arrangement provided with an enclosure is slightly displaceable in the main structure. This ensures that the enclosure remains intact even when adapting the ophthalmological implant.

Favorably, the at least one color pigment is opaque. Preferably, said at least one color pigment is light-sensitive. The at least one color pigment is made of photosensitive substances such as pyrenes, oxazines and/or fulgides, for example. It may, however, also be formed by a metal oxide or non-metal solid substances. Favorably, a plurality of color pigments having different colors are provided. In particular, the ophthalmological implant is similar to a natural iris, which permits an aesthetic rehabilitation.

Favorably, the at least one color pigment, more preferably a plurality of, more preferably most, more preferably all of the color pigments have a tensile extension behavior, which differs from a tensile extension behavior of the enclosure and/or the main structure in particular greatly. For example, there is a difference in the modulus of elasticity, the tensile strength and/or the deformability. In particular, the at least one color pigment has a stiffness, in other words a resistance to elastic deformation, which is at least 50% greater, preferably at least 100% greater than the stiffness or the resistance to elastic deformation of the enclosure and/or the main structure.

The main structure in particular has a variable degree of transmission, wherein preferably the degree of transmission of the main structure when the ophthalmological implant is exposed to light decreases with increasing intensity of the light.

It is advantageous if the main structure is in the shape of a circular ring. Favorably, it has an external diameter, which is reducible for adapting it to the individual anatomical conditions of the eye to be treated. It is expedient if the ophthalmological implant is elastically deformable for implantation.

The central aperture is preferably circular. It is in particular configured such as to be permeable to fluid. It is expedient if the central aperture is permeable to light and has in particular a high degree of transmission. The degree of transmission is in particular greater than 0.9.

Favorably, the enclosure is a thin-wall enclosure. It is made of an enclosure material. It is advantageous if there is a chemical and/or a physical bond between the enclosure material and the main structure material.

The at least one color pigment of the respective pigment arrangement, which is completely enclosed by the enclosure is extremely easy to produce. An ophthalmological implant of this type has exceptional biocompatibility even after adapting the external dimensions thereof.

Favorably, in a preferred embodiment, the enclosure has an enclosure thickness, which is much smaller than a dimension, in particular a height, width, length and/or thickness, of the at least one color pigment of the respective pigment arrangement.

As regards the enclosure thickness, which is between 0.1 μm and 10 μm in each case, deviations often occur as a result of the manufacturing process.

The biocompatible material of the enclosure favorably is/has a polymer material such as, in particular high-purity, silicone, acrylate, and/or methacrylate. It is expedient if the enclosure is made of the biocompatible material entirely. The biocompatible material is preferably arranged in at least one monolayer of the enclosure. It then forms the enclosure material.

The reactive monomers provided in particular on an outside of the enclosure are preferably arranged in at least one reactive layer of the enclosure. The ophthalmological implant is provided with said reactive layer preferably during production thereof.

It is advantageous if the fibers provided in particular on an outside of the enclosure are entangled with a matrix, which is in particular formed by the biocompatible material. Favorably, the fibers form an outer layer of the enclosure. The fibers are preferably arranged in an outermost layer of the enclosure. They are preferably made of a biocompatible material such as silicone, acrylate and/or methacrylate. Favorably, the fibers each have a length of at least 25 µm. It is advantageous if the thickness of the fibers is in each case smaller than 5 µm. It is advantageous if the length/diameter ratio of the fibers is between 3:1 and 7:1. Favorably, there is a physical bond between the enclosure and the main structure material.

In a preferred embodiment, each pigment arrangement has a circumferential diameter, which is smaller than 30 µm, more preferably smaller than 10 µm. Favorably, the design of the at least one color pigment of the respective pigment arrangement is randomly selectable.

The ophthalmological implant configured such that the pigment arrangements are arranged such as to overlap each other at least partly is favorably opaque in the region of the partially overlapping pigment arrangements substantially in a viewing direction of the ophthalmological implant.

In a preferred embodiment, the main structure is formed by a main structure material and the enclosure is formed by an enclosure material, with the main structure material and the enclosure material differing from one another. For example, the main structure material and the enclosure material differ in terms of their composition, density, permeability to light and/or light absorption.

The embodiment of the color pigment and/or the enclosure according to another preferred embodiment results in a particularly high biocompatibility of the ophthalmological implant. The enclosure material is favorably harder, in particular much harder, than the main structure material. Therefore, it in particular has a higher mechanical resistance to a mechanical penetration of another body than the main structure material. This greater hardness is achieved, for example, by a higher linking degree, in particular crosslinking degree, and/or a different material composition. The at least one color pigment is favorably harder, in particular much harder, than the main structure material. Therefore, it in particular has a higher mechanical resistance to a mechanical penetration of another body than the main structure material.

As in particular the at least one color pigment including the associated enclosure is harder, in particular much harder, than the main structure or the main structure material, it is ensured that even if the ophthalmological implant needs to be adapted to the individual anatomical conditions of an eye to be treated, this pigment arrangement within the main structure yields to an adapting or reduction tool such as a pair of scissors, a trepan or a scalpel such that the enclosure remains intact.

Alternatively, for example, only the enclosure is harder than the main structure. The at least one color pigment has a lower hardness than the main structure. Alternatively, the hardness of the at least one color pigment is equal to the hardness of the main structure.

The ophthalmological implant configured such that at least most, preferably, the entirety, of one color pigment at a time is enclosed by its own enclosure has a particularly high biocompatibility. This is particularly true if each color pigment is completely enclosed. Even if the ophthalmological implant needs to be adapted to the individual anatomical conditions of the eye to be treated, this particularly high biocompatibility is provided.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
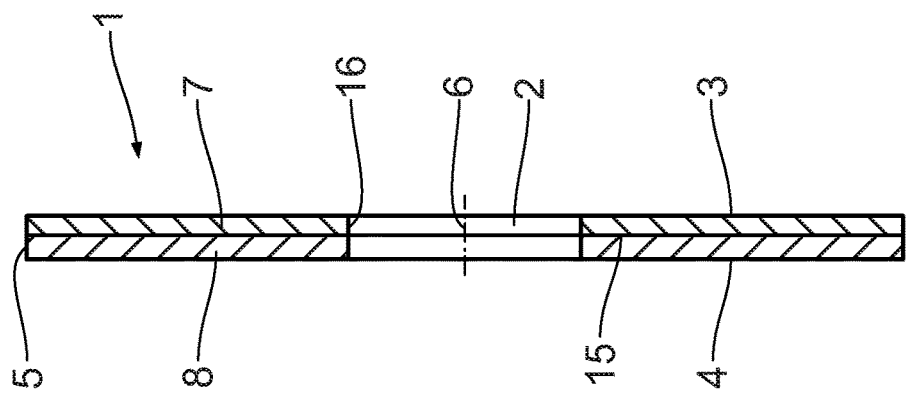
FIG. 2 is a longitudinal sectional view, taken along section line II-II, of the ophthalmological implant shown in FIG. 1.
Figure 1:
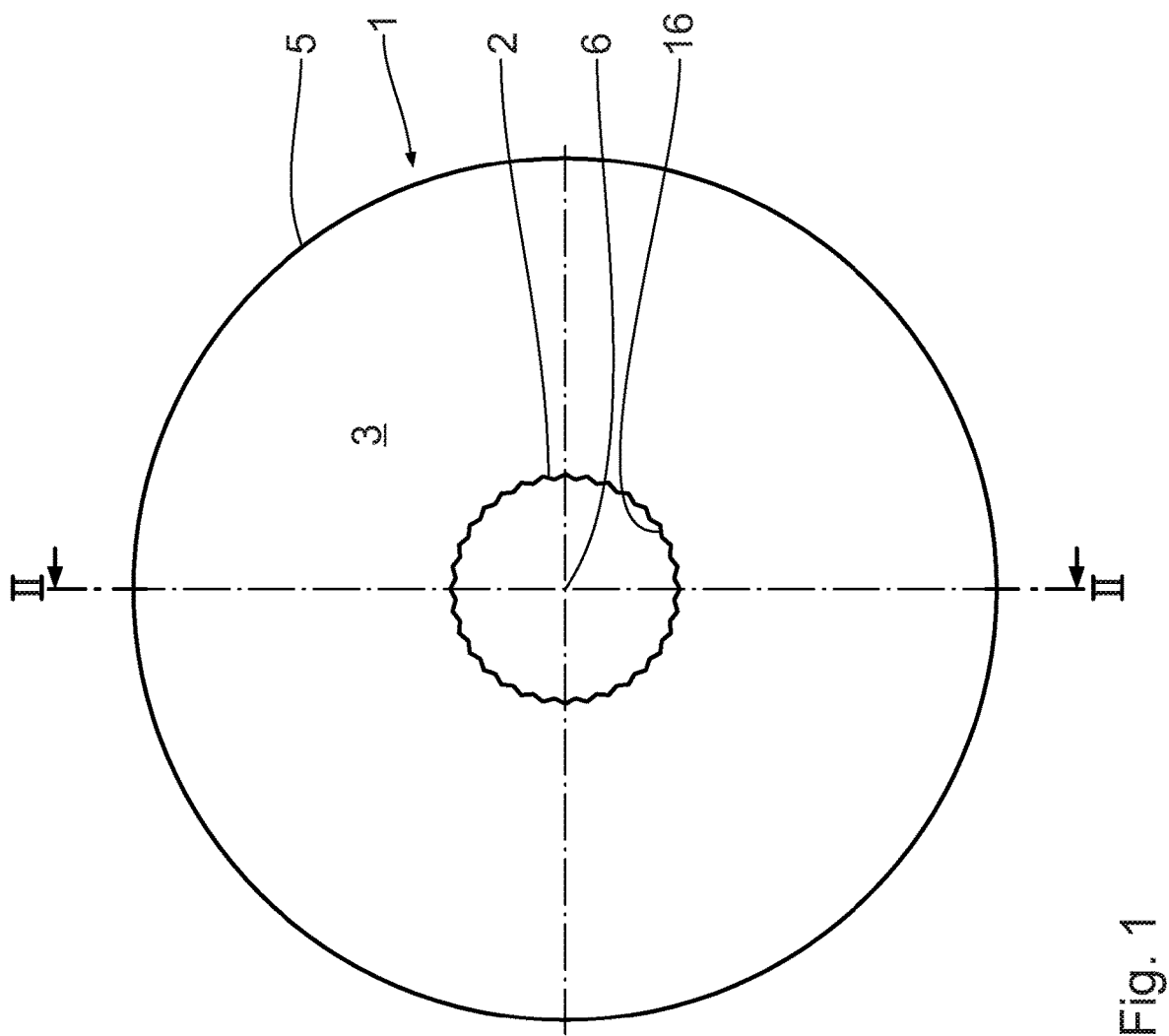
FIG. 1 is a front view of an ophthalmological implant according to the invention.
Figure 4:
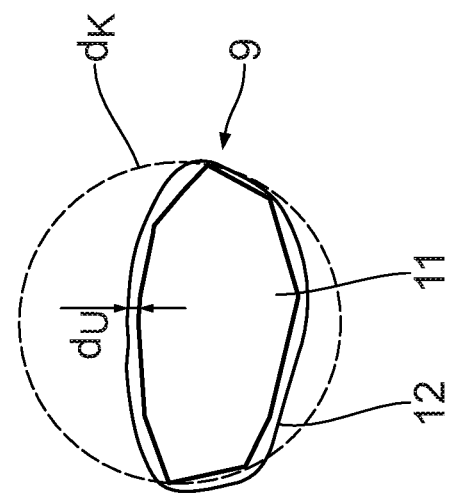
FIG. 4 is an enlarged view of a pigment arrangement of the ophthalmological implant shown in FIGS. 1 and 2.
Figure 3:
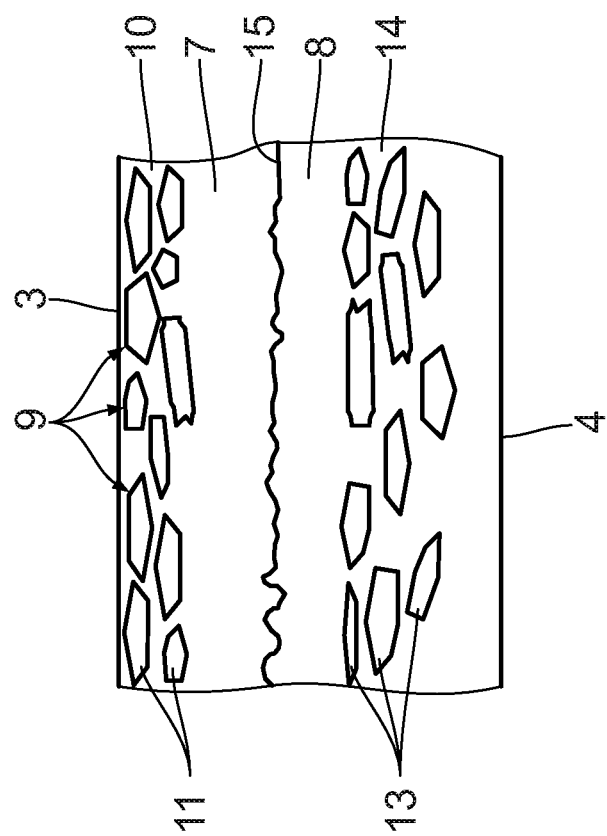
FIG. 3 is an enlarged partial sectional view of the ophthalmological implant shown in FIGS. 1 and 2.

An ophthalmological implant shown in its entirety in FIGS. 1 and 2, which in particular reproduces a natural iris, comprises an annular main structure 1 with a central, substantially circular aperture 2.

The main structure 1 has a substantially flat design and has a front side 3 and a rear side 4 arranged opposite the front side 3. The front side 3 is favorably plane or smooth. It is advantageous if the main structure 1 has a structured surface on the front side 3, which resembles that of a natural iris. It is advantageous if the rear side 4 is in particular plane or smooth. Alternatively, the front side 3 and/or the rear side 4 have a slightly convex envelope.

At its periphery, the main structure 1 is externally delimited by an edge face, which surrounds a central axis 6 of the main structure 1. The main structure 1 has an external diameter, which amounts to at least 10 mm, in particular at least 12 mm. The external diameter is reducible by trepanning, for example. When doing so, a sharp hollow punch the internal diameter of which corresponds to the desired external diameter of the ophthalmological implant is used to cut off an excess circular ring. This allows the size of the ophthalmological implant to be flexibly adapted to the respectively desired size.

The main structure 1 has a thickness in the direction of the central axis 6, which is between 0.1 mm and 0.4 mm.

The aperture 2 has a diameter in the range of 1 mm to 8 mm, in particular of 3 mm to 5 mm. It is in particular configured as a free opening.

At its periphery, the aperture 2 is delimited by an inner edge face 16. The inner edge face 16 is in particular rough and has small notches and projections, which are arranged in an alternating configuration.

The main structure 1 is a multi-ply structure, namely a two-ply structure in this embodiment. It comprises a front ply 7 and a rear ply 8. The plies 7, 8 are arranged along the central axis 6 in such a way that the front ply 7 includes or forms the front side 3 while the rear ply 8 includes or forms the rear side 4.

The front ply 7 is preferably made of silicone. The rear ply 8 is preferably made of silicone. Other polymerizable substances are alternatively conceivable. A plurality of pigment arrangements 9 is embedded in the front ply 7. The entire front ply 7 is impermeable to light preferably at least partly. The pigment arrangements 9 in the front ply 7 are favorably arranged in an outer layer 10 of the front ply 7, in other words adjacent to the front side 3.

They overlap partly in the direction of the central axis 6 and/or perpendicular thereto. The pigment arrangements 9 are designed with different colors. Each pigment arrangement 9 has an inner color pigment 11 and an outer enclosure 12, which encloses the color pigment 11 completely. The pigment arrangements 9 each have a circumferential diameter $d_K$, which is smaller than 30 μm, more preferably smaller than 10 μm.

The enclosures 12 preferably have a substantially uniform enclosure thickness $d_U$. The enclosures 12 are entirely made of a biocompatible polymer material such as silicone, acrylate and/or methacrylate. Favorably, the enclosures 12 and the main structure 1, in particular the front ply 7 thereof, are usually made of an identical material. Preferably, two-component silicone is used to produce them.

Favorably, the enclosures 12 have reactive monomers at least one their outsides, said reactive monomers being capable of reacting with surrounding monomers in such a way as to form a chemical bond.

In an alternative, preferred embodiment, the enclosures 12 are configured as fibers at least on the outside thereof. The fibers are entangled with a surrounding matrix of the biocompatible material of the respective enclosure 12, which results in a stable mechanical and/or physical bond. An embodiment without fibers is conceivable.

The pigment arrangements 9 are produced, for example, by dispersing pure color pigments 11 in a low concentration with high-purity, liquid biomaterial. The concentration of the color pigments 11 is then increased by filtration of the liquid biomaterial. The high-concentration color pigments 11 enclosed in this manner are stored under conditions that ensure a further processing throughout the storage period.

The rear ply 8 contains pigments 13, which are arranged in a layer 14. The pigments 13 are capable of absorbing visible light. They are favorably black. Alternatively, the pigments 13 correspond to the color pigments 11.

The plies 7, 8 differ in particular in terms of the concentration and/or the type of the pigments 11, 13 used.

Between the plies 7, 8, there is a boundary surface 15, which is corrugated or smooth. In a corrugated configuration, the corrugations favorably have a height, which is greater than 0.025 mm, more preferably greater than 0.05 mm, more preferably greater than 0.1 mm.

The boundary surface 15 may be part of a boundary region, in which there is a gradual transition in terms of the concentration and/or type of the pigments 11, 13 used between the front ply 7 and the rear ply 8. The boundary region has a thickness of at least 0.025 mm, more preferably of at least 0.05 mm, more preferably of at least 0.1 mm.

When all of the color pigments 11 are enclosed, the surface of the color pigments 11 is in no/virtually in no direct contact with tissue or aqueous humour of the eye even after adapting the external diameter of the opthalmological implant but is sealed off completely in particular by the respective enclosure 12 of biocompatible material. An insufficient biocompatibility of the ophthalmological implant can thus be avoided.

For implanting the ophthalmological implant, the main structure 1 is arranged in a capsular bag, in a posterior chamber or in an anterior chamber of the eye with its front ply 7 facing a cornea of the eye. The edge face 5 is supported against the sulcus. The central axis 6 runs parallel to the optical axis of a natural ocular lens, and in particular coincides with the latter. In order to secure the ophthalmological implant in the eye, the main structure 1 is sutured with the capsular bag, the ciliary body, the iris root or the sclera, in particular with sutures of a fatigue-resistant suture material.

According to an alternative embodiment, the main structure 1 has more than two plies or precisely one ply. Alternatively, the front ply 7 and/or the rear ply 8 consist of multiple plies.

While specific embodiments of the invention have been shown and described in detail to illustrate the application of the principles of the invention, it will be understood that the invention may be embodied otherwise without departing from such principles.

The invention claimed is:

1. An ophthalmological implant, comprising:
  a main structure comprising a central aperture, a first side and a second side arranged opposite the first side, the main structure having a thickness between 0.1 mm and 0.4 mm; and
  a plurality of pigment arrangements arranged in the main structure, wherein each of the pigment arrangements has an inner color pigment and an outer enclosure completely enclosing the color pigment, the enclosure of each pigment arrangement having an enclosure outer shape, at least one color pigment of the each pigment arrangement has a color pigment outer shape, wherein the enclosure outer shape corresponds to the color pigment outer shape of the at least one color pigment of each pigment arrangement;
  a material of the enclosures being harder than a material of the main structure;
  the enclosures having a uniform enclosure thickness;
  the main structure having a thickness which is between 0.1 mm and 0.4 mm.

2. An ophthalmological implant as claimed in claim 1, wherein the material of the main structure and the material of the enclosures are configured to yield to a tool adapting the ophthalmological implant, the material of the enclosures being biocompatible material.

3. An ophthalmological implant as claimed in claim 1, wherein the enclosures have an enclosure thickness, which is smaller than a dimension of the color pigment of a respective pigment arrangement.

4. An ophthalmological implant as claimed in claim 1, wherein the enclosures have an enclosure thickness, which is between 0.1 μm and 10 μm in each case.

5. An ophthalmological implant as claimed in claim 1, wherein the enclosures have biocompatible material.

6. An ophthalmological implant as claimed in claim 1, wherein the enclosures comprise reactive monomers.

7. An ophthalmological implant as claimed in claim 6, wherein the reactive monomers are provided on an outside of the enclosures.

8. An ophthalmological implant as claimed in claim 1, wherein each of the plurality of pigment arrangements has a circumferential diameter less than 30 μm.

9. An ophthalmological implant as claimed in claim 1, wherein the plurality of pigment arrangements are arranged in at least one layer of the main structure.

10. An ophthalmological implant as claimed in claim 1, wherein the plurality of pigment arrangements are arranged such the plurality of pigment arrangements at least partly overlap each other.

11. An ophthalmological implant as claimed in claim 1, wherein the main structure is formed by a main structure material and the enclosures are formed by an enclosure material, wherein the main structure material and the enclosure material differ from one another.

12. An ophthalmological implant as claimed in claim 1, wherein the color pigment is harder than the material of the main structure.

13. An ophthalmological implant as claimed in claim 1, wherein the main structure has a multi-ply design.

14. An ophthalmological implant as claimed in claim 1, wherein each of the plurality of pigment arrangements has a circumferential diameter less than 10 μm.

15. An ophthalmological implant, comprising:
a main structure comprising a central aperture, a first side and a second side arranged opposite the first side; and
a plurality of pigment arrangements arranged in the main structure, wherein each of the pigment arrangements has an inner color pigment and an outer enclosure completely enclosing the inner color pigment, each of the enclosures having an enclosure thickness, which is between 0.1 μm and 10 μm in each case;
a material of the enclosures being harder than a material of the main structure;
the enclosures having a uniform enclosure thickness;
the main structure having a thickness which is between 0.1 mm and 0.4 mm.

16. An ophthalmological implant, comprising:
a main structure comprising a central aperture, a first side and a second side arranged opposite the first side, the main structure having a thickness which is between 0.1 mm and 0.4 mm; and
a plurality of pigment arrangements arranged in the main structure, wherein each of the pigment arrangements is separate, and has an inner color pigment and an outer enclosure individually and completely enclosing the respective inner color pigment, a material of the enclosure being harder than a material of the main structure, the enclosures having a uniform enclosure thickness, each of the plurality of pigment arrangements having a circumferential diameter less than 30 μm.

17. An ophthalmological implant in accordance with claim 16, wherein:
the material of the main structure and the material of the enclosures are configured to arrange each of the plurality of pigment arrangements displaceable in the main structure when reducing a size of the ophthalmological implant, the material of the enclosure being biocompatible material.

18. An ophthalmological implant in accordance with claim 16, wherein:
the material of the main structure and the material of the enclosures are configured to cause the plurality of pigment arrangements to yield to a reduction tool when reducing a size of the ophthalmological implant, the material of the enclosure being biocompatible material, each of the plurality of pigment arrangements being separate from each other in the material of the main structure.

* * * * *